United States Patent [19]

Koning et al.

[11] Patent Number: 4,716,887
[45] Date of Patent: Jan. 5, 1988

[54] APPARATUS AND METHOD FOR ADJUSTING HEART/PACER RATE RELATIVE TO CARDIAC $PCO_2$ TO OBTAIN A REQUIRED CARDIAC OUTPUT

[75] Inventors: Gerrit Koning, Vries, Netherlands; Edward A. Schroeppel, Miamar, Fla.

[73] Assignee: Telectronics N.V., Curacao, Netherlands Antilles

[21] Appl. No.: 722,575

[22] Filed: Apr. 11, 1985

[51] Int. Cl.[4] ............................................. A61N 1/36
[52] U.S. Cl. .............................. 128/419 PG; 128/635
[58] Field of Search .................... 128/635, 2, 419 PG

[56] References Cited

U.S. PATENT DOCUMENTS

| | | | |
|---|---|---|---|
| 3,572,315 | 3/1971 | Cullen, II | 128/2 |
| 3,658,053 | 4/1972 | Fergusson et al. | 128/2 G |
| 3,659,586 | 5/1972 | Johns et al. | 128/2 E |
| 3,710,778 | 1/1973 | Cornelius | 128/2 G |
| 3,900,382 | 8/1975 | Brown, Jr. | 128/635 |
| 4,009,721 | 3/1977 | Alcidi | 128/419 PG |
| 4,133,735 | 1/1979 | Afromowitz et al. | 128/642 |
| 4,197,853 | 4/1980 | Parker | 128/635 |
| 4,202,339 | 5/1980 | Wirtzfeld et al. | 128/419 PG |
| 4,218,298 | 8/1980 | Shimada et al. | 128/635 |
| 4,252,124 | 2/1981 | Maurer et al. | 128/635 |
| 4,273,636 | 6/1981 | Shimada et al. | 128/635 |
| 4,305,802 | 12/1981 | Koshiishi | 128/635 |
| 4,401,122 | 8/1983 | Clark, Jr. | 128/635 |
| 4,404,972 | 9/1983 | Gordon et al. | 128/419 PG |
| 4,409,980 | 10/1983 | Yano et al. | 128/635 |
| 4,411,741 | 10/1983 | Janata | 204/1 T |
| 4,450,842 | 5/1984 | Zick et al. | 128/635 |
| 4,474,183 | 10/1984 | Yano et al. | 128/635 |
| 4,478,222 | 10/1984 | Koning et al. | 128/632 |
| 4,488,556 | 12/1984 | Ho | 128/635 |
| 4,535,774 | 8/1985 | Olson | 128/419 PG |

FOREIGN PATENT DOCUMENTS 2442631  8/1980  France ............... 128/419 PG

OTHER PUBLICATIONS

Guyton, *Textbook of Medical Physiology-Fifth Edition*, published by W. B. Saunders Co.-Philadelphia/London/Toronto, ©1976, pp. 543-556.
Parker et al., "Catheter Tip Electrode for Continuous Measurement of $pO_2$ and $pCO_2$", *Med. & Biol. Eng. & Comput*, Sep. 1978, vol. 16, No. 4, pp. 599-600.

*Primary Examiner*—William E. Kamm
*Attorney, Agent, or Firm*—Henry W. Collins; Thomas R. Vigil

[57] ABSTRACT

The apparatus for pacing a heart in accordance with the heart rate needed to produce a required cardiac output relative to the partial pressure of carbon dioxide in the blood, $pCO_2$, while the person is exercising comprises a pacer adapted to be implanted in a human body and having a pulse generator and control circuitry (e.g. including a microprocessor) therein, a pacing lead adapted to be implanted in a heart and having a distal electrode adapted to engage and supply pacing pulses to a right ventricle of a heart and a $pCO_2$ sensor for sensing $pCO_2$ of the blood in the heart. An algorithm and routine utilizing same are stored in the control circuitry (microprocessor) and are adapted to relate $pCO_2$ with the required heart rate or change in rate, $\Delta R$, needed to supply a desired cardiac output and to cause the pacer to pace the heart at the required heart rate when the heart is not naturally paced.

22 Claims, 10 Drawing Figures

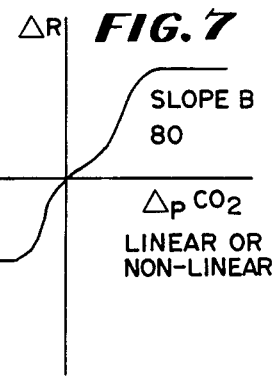
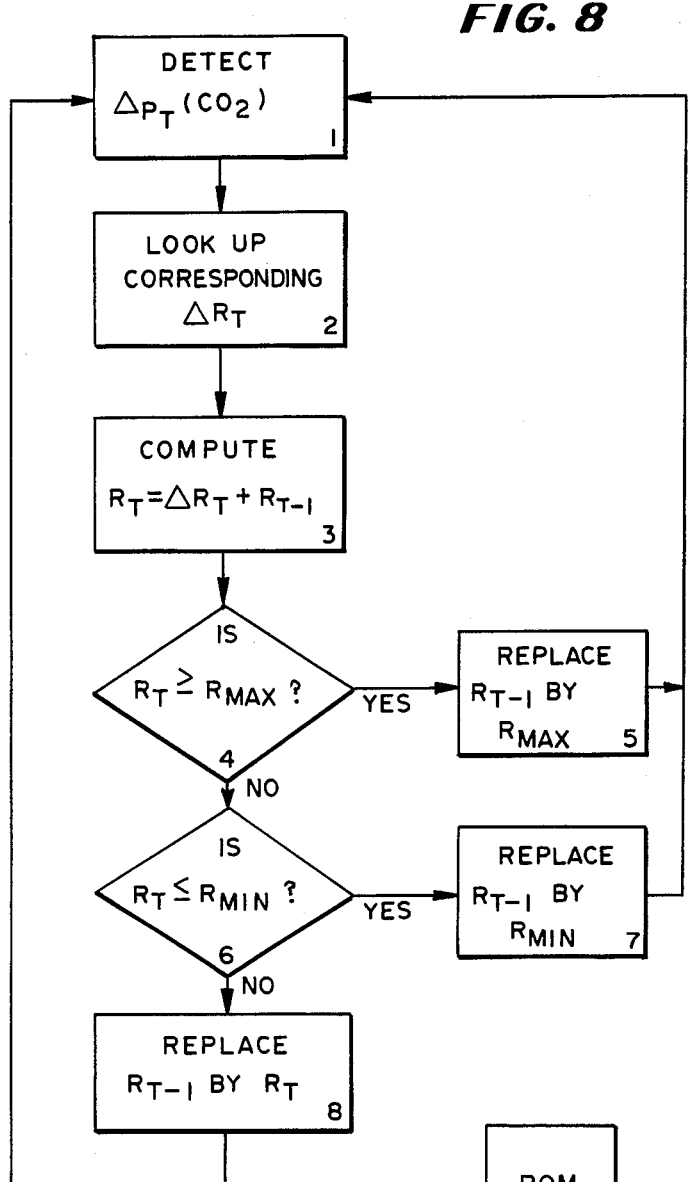
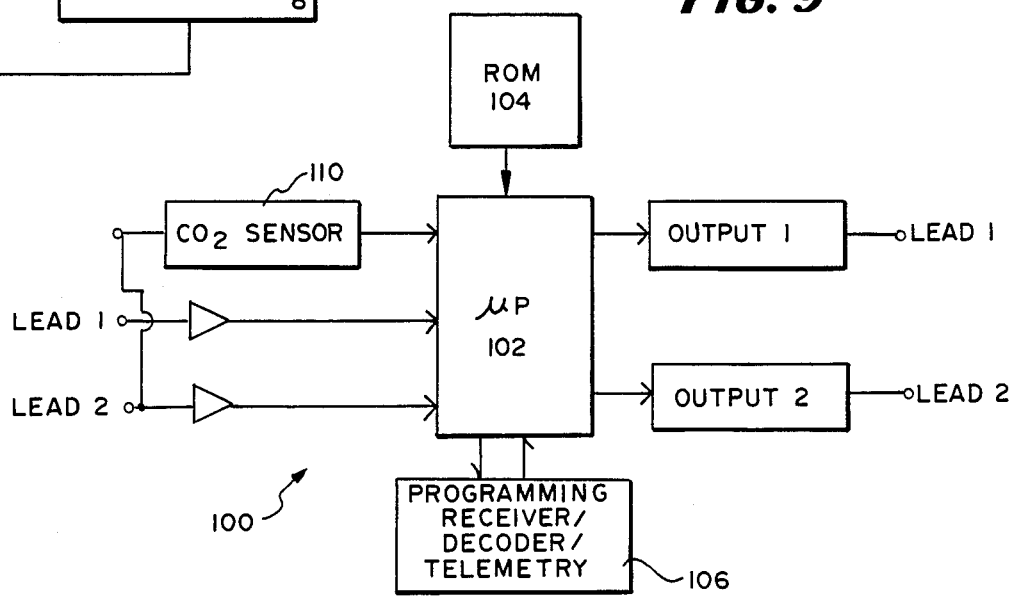

APPARATUS AND METHOD FOR ADJUSTING HEART/PACER RATE RELATIVE TO CARDIAC PCO₂ TO OBTAIN A REQUIRED CARDIAC OUTPUT

BACKGROUND OF THE INVENTION

1. Field of the Invention

The present invention relates to a pacer system which is adapted to alter the rate of the pacer pulses delivered (rate of pacing pulses delivered by an artificial pacemaker) to a heart while an individual is exercising relative to, and utilizing, the partial pressure of carbon dioxide, $pCO_2$, in the blood in a heart to obtain a required cardiac output.

2. Description of the Prior Art

Heretofore patients with heart dysfunctions or heart disease such as sinus node disease have been able to live a relatively normal life with the implantation of an artificial pacemaker often referred to as a pacer. However, such pacers have not always been able to mimic the response of a normal healthy heart. A normal heart responds to exercise and stress by increasing cardiac output through increased heart rate and/or stroke volume.

In this respect, patients with sinus node disease have lost the ability to increase heart rate with exercise. Accordingly, it has become a goal of optimal pacing to provide exercise responsiveness in a pacer by sensing the need for increased cardiac output.

With a view towards obtaining this goal, a number of pacemakers have been proposed for indirectly sensing the need for increased heart rate by sensing P-waves, nerve impulses, Q-T interval, pH, oxygen saturation, respiratory rate, stroke volume, motion, atrial pressure and temperature.

A P-wave triggered artificial pacemaker adapted to be exercise responsive by responding to average atrial rate is proposed in the Knudson & Amundson U.S. Pat. No. 4,313,442.

An artificial pacemaker responsive to changes in the Q-T interval is proposed in the Rickards U.S. Pat. No. 4,228,803.

The Heilman et al. U.S. Pat. No. 4,303,075 discloses a method and apparatus for maximizing stroke volume through AV pacing using an implanted cardioverter/pacer which is programmed with an AV delay tailored to the particular patient. The mechanism detects and processes the impedance of the heart across two electrodes in contact with heart muscle during each heart cycle and uses the changes from cycle to cycle to trigger the issuance of pulses from the pacer depending on the direction of the impedance changes to maximize stroke volume of the heart, which is proportional to the change in value of impedance between the minimum and maximum detected impedance per heart cycle.

The Funke U.S. Pat. No. 4,312,355 discloses a dual pace-dual sense cardiac pacer which is able to stimulate the atrium and/or the ventricle and which is able to entrain the ventricle, when the atrial rate increases, while preventing bradycardic episodes. The pacer action is triggered by detection of naturally occurring atrial and ventricular action or pulses within a predetermined time period.

The Roline U.S. Pat. No. 4,363,325 discloses a multiple mode pacer activated to switch modes relative to heart rate while preventing atrial bradycardia. This is achieved by mode switching of the pacer from an atrial synchronous mode to a ventricular inhibited mode. Such switch of modes is actuated when no atrial activity is sensed within a preset escape interval referred to as a hysteresis period. Reversal of the mode back to the atrial synchronous mode from the ventricular inhibited mode is actuated in response to a detected atrial rate which is higher than a preset, lower, ventricular rate. With this mode switching, the ventricle will not be stimulated twice in quick succession, which overstimulation could cause atrial bradycardia.

A proposal for placing electrodes on the Hering's nerve which extends from receptors in the sinus and glomus carotids is disclosed in the Gonzalez U.S. Pat. No. 4,201,219.

Sensors for sensing blood pH are proposed in the Alcidi U.S. Pat. No. 4,009,721 and the Mauer et al U.S. Pat. No. 4,252,124. Alcidi controls a pacer relative to the level of blood pH sensed.

In the Bornzin U.S. Pat. No. 4,467,807 molecular oxygen is sensed with an oxygen sensor, preferably of the type as disclosed in the Wirtzfeld et al U.S. Pat. Nos. 4,202,339 and 4,299,820. The Wirtzfeld et al patents teach measuring of oxygen saturation of blood using optical techniques. The transmissiveness of light through blood is used by Wirtzfeld et al to measure oxygen concentration. Bornzin teaches using such measurements for controlling the pacing of a heart.

See also the article "A new pacemaker autoregulating the rate of pacing in relation to metabolic needs+ by Cammilli, Alcidi and Papeschi which appeared in "Cardiac Pacing", pages 414–419 Amsterdam-Oxford: Excerpta Medica, 1977 which teaches sensing pH in the right atrium.

Another artificial cardiac pacemaker which increases pacing rate in accordance with an increase in respiration rate is proposed in the Krasner U.S. Pat. No. 3,593,718.

Pacers for sensing motion or mechanical activity are proposed in the Dahl U.S. Pat. No. 4,140,132 and the Anderson et al U.S. Pat. No. 4,428,378.

The Denniston III U.S. Pat. No. 3,815,611 discloses an apparatus which detects muscle contractions through impedance measurement. The device includes an elastomer body whose impedance changes when flexed. The elastomer body is positioned adjacent a muscle such as a heart muscle such that when the muscle contracts, the elastomer body is flexed to provide a change in impedance to a bias voltage supplied thereto. Such electrical signal can be used to control a pulse generator to generate a pulse when a specified period of time has elapsed since the latest heart activity was sensed by the elastomer body.

Heretofore it has been proposed in the Cohen U.S. Pat. No. 3,358,690 to sense pressure in the right atrium and to utilize the pressure sensed to control pacing of an electrode in the right ventricle.

Also, the Zacouto U.S. Pat. No. 3,857,399 discloses, in FIG. 19 thereof, a pressure sensor that measures either left ventricular pressure or intramyocardial pressure. One sensor is located in the left ventricle. Apparently, the pacer coupled to these sensors responds to average base pressure over relatively long periods of time and the pacer system disclosed therein appears to be static and slowly responsive to exercise.

The Sjostrand et al. U.S. Pat. No. 3,650,277 discloses a system for reducing and controlling the blood pressure of a hypertensive patient by electrical stimulation of the carotid sinus nerves, one of the baroreceptor centers of the body. The system incorporates a pressure transducer which is connected to or applied to an artery of a patient and provides electrical signals substantially representing the instantaneous arterial blood pressure of a patient. Upon calculation of a mean arterial pressure, the system is utilized to provide a series of electrical pulses having a predetermined frequency, magnitude and amplitude through an afferent nerve, such as the carotid sinus nerve, to the heart to mimic pulses to the heart occurring naturally in patients having normal blood pressure. These pulses are provided during the first portion of each heart cycle to take over the function of controlling blood pressure that is usually provided by normally functioning baroreceptors in patients who are not hypertensive.

Another artificial cardiac pacemaker which is responsive to exercise by sensing venous blood temperature in the right ventricle of the heart is proposed in the Cook et al U.S. Pat. No. 4,436,092.

As pointed out in the Alcidi U.S. Pat. No. 4,009,721, when an individual is engaging in muscular work or exerting a muscular effort, such as during exercise, the pH, the $pO_2$ and the $pCO_2$ of the human blood undergo a modification. More specifically, the pH and the $pO_2$ decrease and the $pCO_2$ increases. In view of this fact, Alcidi proposed monitoring the pH of the blood in the right atrium and regulating the rate of stimulating pulses from a pacemaker in relation to the instantaneous variation of the pH of the blood.

In man, however, the pH range of blood is fairly narrow banded as noted in the Maurer et al U.S. Pat. No. 4,252,124. Typically, the pH value for man is between 7.36 and 7.43.

The extreme values for pH in the human organism are typically given as pH 6.8 and pH 7.8. If the pH value deviates from this range serious disturbances can arise which can lead to brain damage and to death. For example, the pH value is lowered (acidosis) due to oxygen deficiency, in the case of kidney failure or a diabetic coma.

On the other hand, the pH value is increased (alkalosis) during exercise and in the case of excess breathing of oxygen in conjunction with anaesthesia or in the case of a lasting acid loss such as occasioned by vomiting.

Thus, measuring the pH changes in blood, although perhaps primarily related to change in $pCO_2$, is also affected by other factors unrelated to exercise.

As will be described in greater detail hereinafter, the apparatus of the present invention differs from the artificial pacemaker proposed in the Alcidi U.S. Pat. No. 4,009,721 by utilizing an ion sensitive field effect transistor (ISFET) which is mounted on a pacing lead near the tip of the pacing lead and which includes a gas permeable membrane over a solution-filled chamber which is located above the base or gate region of the ISFET.

Further, the method for using the apparatus of the present invention differs from the mode of operation of the Alcidi artificial pacemaker by providing for operation of the apparatus between maximum and minimum pacing/heart rates, relative to the partial pressure of $CO_2$ ($pCO_2$) in the blood independent of the pH of the blood.

In the sensing of $pCO_2$ in a fluid such as blood, one typically measures or senses the pH and relates the pH to $pCO_2$. In this respect, the following relationship occurs in blood containing oxygen and carbon dioxide:

$$H_2O + CO_2 \rightleftharpoons H^+ + HCO_3-$$

Heretofore, it has been proposed to provide percutaneous carbon dioxide sensors with a $CO_2$ permeable membrane. In such sensors placed against the skin, $CO_2$ gas diffusing through the skin passes through the gas permeable membrane and into a chamber within the sensor where a pH sensing electrode is in communication with the liquid in the chamber. As the amount of $CO_2$ in the liquid increases, the amount of the positive free hydrogen ions increases. These ions collect at the pH sensing electrode causing changes in electrical potential. The changes in electrical potential are then utilized to determine the amount of $CO_2$ gas in the blood.

Examples of percutaneous $CO_2$ sensors are disclosed in the following patents:

| U.S. PAT. NO. | PATENTEE |
| --- | --- |
| 3,659,586 | Johns et al |
| 4,197,853 | Parker |
| 4,401,122 | Clark, Jr. |

It has also been proposed to provide catheters insertable into a blood vessel with a gas permeable membrane and pH sensor for measuring gases in the blood. Examples of such previously proposed catheters are disclosed in the following patents:

| U.S. PAT. NO. | PATENTEE |
| --- | --- |
| 3,572,315 | Cullen II |
| 3,658,053 | Fergusson et al |
| 3,710,778 | Cornelius |

Further, it has been proposed to utilize field effect transistors for measuring chemical properties such as ion activities, including gas ions. Such field effect transistors have taken various forms such as a chemical sensitive field effect transistor (CHEMFET), an ion sensitive field effect transistor (ISFET), an insulated-gate field effect transistor (IGFET), a liquid oxide semiconductor field effect transistor (LOSFET), and a conventional metal oxide semiconductor field effect transistor (MOSFET). Examples of such previously proposed field effect transistors are disclosed in the following patents:

| U.S. PAT. NO. | PATENTEE |
| --- | --- |
| 4,020,830 | Johnson et al |
| 4,180,771 | Guckel |
| 4,198,851 | Janata |
| 4,218,298 | Shimada et al |
| 4,273,636 | Shimada et al |
| 4,411,741 | Janata |
| 4,478,222 | Koning et al |
| 4,486,290 | Cahalan et al |

The Janata U.S. Pat. No. 4,411,741 discloses a gap between a bridge member with holes in it over an insulator over a conducting channel or gate region of a CHEMFET.

Also, a solid state reference electrode capable of use with a field effect transistor, such as an ISFET, has been proposed in the Zick et al U.S. Pat. No. 4,450,842 and an AC mode of operating a CHEMFET is disclosed in the Ho U.S. Pat. No. 4,488,556.

Although some of the FETs disclosed in the above patents have a chemically sensitive layer over a gate region of the FET, these patents do not appear to disclose a chamber with a liquid solution therein over a gate region of a FET with a $CO_2$ permeable membrane closing off the chamber and being adapted to be exposed to blood as provided in the apparatus of the present invention.

SUMMARY OF THE INVENTION

According to the invention, there is provided an implantable apparatus for pacing a heart in accordance with the heart/pacer rate needed to produce a required cardiac output relative to the partial pressure of carbon dioxide in blood, $pCO_2$, while the person having the apparatus implanted within his body is exercising comprising:

a pacer adapted to be implanted in the human body and having a pulse generator and control circuitry therein;

a pacing lead adapted to be implanted in a heart and adapted to be coupled to said pacer, said pacing lead having a tip electrode adapted to engage and supply pacing pulses to a ventricle of a heart and having an opening therein in a portion of the lead received in the heart;

$pCO_2$ sensing means mounted in said opening; and said control circuitry including means for relating a current of the $pCO_2$ sensing means to the partial pressure of carbon dioxide, $pCO_2$, in the blood, for determining the required pacing rate needed to supply a desired cardiac output relative to the $pCO_2$ measured, and for causing the Pacer to pace the heart at the required rate when the heart is not naturally paced while the person is exercising.

Preferably, the electronic $pCO_2$ sensor comprises an ion sensitive field effect transistor (ISFET) which is mounted in the pacing lead beneath the opening and which includes a silicon bulk having a middle surface area defining a gate region of said ISFET and facing the opening;

a liquid solution over the gate region;

a $CO_2$ permeable membrane over the opening and the gate region sealing off the area above the gate region to encapsulate the liquid solution in a chamber formed between the bulk and the membrane above the gate region;

a drain source formed in the silicon bulk;

a source formed in the silicon bulk; and a reference electrode mounted in the chamber;

the drain-source current through the ISFET (assuming the voltage between reference electrode and source is kept constant) being changed by free hydrogen ions in the liquid solution caused by $CO_2$ that passes from the blood through the permeable membrane into the liquid solution, such change in drain-source current being directly related to the change of $pCO_2$ in the blood in the heart via the voltage between the gate and source VGS, versus the drain-source current $I_{DS}$ characteristic of the field effect transistor.

Further, according to the invention there is provided a method for pacing a heart in accordance with the heart rate needed to produce a required cardiac output relative to the partial pressure of carbon dioxide in the blood, $pCO_2$, while a person, whose heart is being paced, is exercising using an apparatus comprising:

a pacer which is adapted to be implanted in the human body and which has a pulse generator and control circuitry;

a pacing lead which is adapted to be implanted in a heart and adapted to be coupled to said pacer, said pacing lead having a tip electrode adapted to engage and supply pacing pulses to a ventricle of the heart and having an opening therein in a portion of the lead received in the heart;

$pCO_2$ sensing means mounted in the opening in the lead, said control circuitry including means for relating a current of said $pCO_2$ sensing means to the partial pressure of carbon dioxide, $pCO_2$, in the blood, for determining the required pacing rate needed to supply a desired cardiac output relative to the $pCO_2$ measured, and for causing the pacer to pace the heart at the required rate when the heart is not naturally paced, said method comprising the steps of:

sensing the $pCO_2$ in a heart with said $pCO_2$ sensing means;

relating the $pCO_2$ sensed with a required heart rate needed to supply a desired cardiac output; and pacing the heart at the required heart rate when the heart is not naturally paced.

BRIEF DESCRIPTION OF THE DRAWINGS

FIG. 7 is a graph of $\Delta R$ versus $\Delta pCO_2$ where the relationship between $\Delta R$ and $\Delta pCO_2$ is linear or nonlinear.

FIG. 8 is a flow chart of a program or routine carried out by the control circuitry (microprocessor) of the apparatus shown in FIG. 1 which uses a look-up table for determining a $\Delta R$ corresponding to a $\Delta pCO_2$ for both linear and nonlinear relationships between changes of heart/pacer rate, $\Delta R$ and $\Delta pCO_2$ as shown in FIG. 7.

FIG. 9 is a schematic circuit diagram of the sensing, detecting, processing and control circuitry which can be used in the apparatus shown in FIG. 1 for controlling pacing rate relative to the $pCO_2$ sensed in the blood in the heart.

DESCRIPTION OF THE PREFERRED EMBODIMENT

Figure 1:
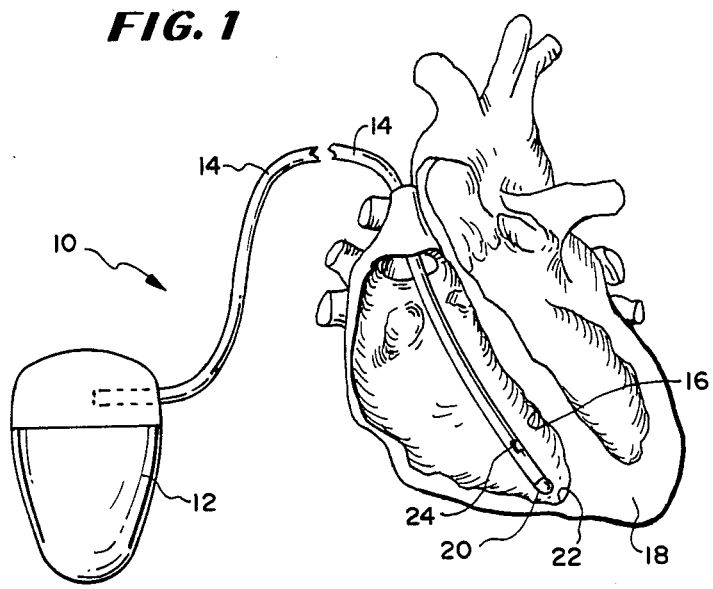
FIG. 1 is a diagram of the apparatus of the present invention for controlling the pacing rate of an implanted artificial pacer in response to $pCO_2$ measured in the right ventricle in accordance with the teachings of the present invention and shows a heart, a pacing lead with a tip electrode thereof located at the apex of the right ventricle of the heart, an ISFET sensor mounted on the pacing lead and positioned near the tip electrode and in the right ventricle, and a pacer containing control circuitry for controlling the pacing rate in response to the $pCO_2$ sensed.

Referring now to the drawings in greater detail, there is illustrated in FIG. 1 an apparatus 10 or pacer system 10 which is constructed according to the teachings of the present invention and which includes an implanted pacer or artificial pacemaker 12 shown in block form. The pacer 12 includes a pulse generator including amplifiers for sensing electrical cardiac activity, and control circuitry typically including a microprocessor.

The pacer 12 is connected to the pacing lead 14 at the proximal end of the lead which extends pervenously into the right ventricle 16 of a heart 18 where a tip electrode 20 at the distal end of the lead 14 engages and stimulates the apex 22 of the right ventricle 16.

In accordance with the teachings of the present invention, a sensor 24 for sensing the partial pressure of carbon dioxide in the blood in the heart, i.e., a $pCO_2$ sensor 24, is mounted on the lead 14 so as to be located in the right ventricle just behind the tip electrode 20. This $pCO_2$ sensor 24 is connected to excitation and detection circuitry in the pacer 12 as will be described in greater detail below.

When a patient with sinus node disease has a pacing system implanted within his or her body with a pacing lead 14 implanted in his or her heart, such as in the right ventricle, such pacing system 10 stimulates the ventricle at a preset rate. In some patients, the heart has lost its ability to increase ventricular rate with exercise. However, as the body engages in muscular activity, especially intense and prolonged muscular activity, the partial pressure of carbon dioxide, $pCO_2$, in the blood increases.

In accordance with the teachings of the present invention, the $pCO_2$ in the blood in the ventricle is sensed by the $pCO_2$ sensor and the amount of $pCO_2$ sensed is used for controlling the rate of application of pulses to the tip electrode 20. This rate is referred to herein as the pacer rate R. Thus, the system 10 uses $pCO_2$ as a measure of exercise level.

Figure 5:
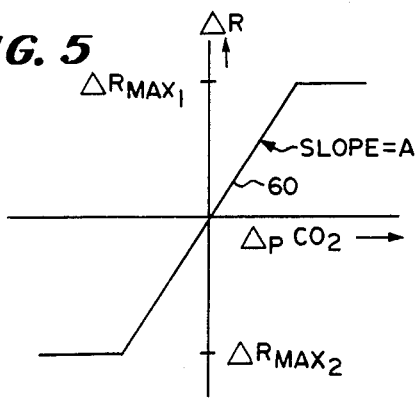
FIG. 5 is a graph showing the change in pacing rate, $\Delta R$, relative to changes in partial pressure of carbon dioxide, $\Delta pCO_2$.

As shown in FIG. 5, the relationship of the change in $pCO_2$, $\Delta pCO_2$, to the change in heart rate, $\Delta R$, can be assumed to be linear with a slope equal to "A". Alternatively, the relationship of $\Delta pCO_2$ to $\Delta R$ can be linear or nonlinear as shown in FIG. 7.

In either event, based upon the relationship between $\Delta pCO_2$ and $\Delta R$, the pacer 12 can be adapted to exercise. More specifically, the rate of pulse generation or pacer rate can be controlled so that the pacing system 10 can be adapted for exercise based on measurements of $pCO_2$ when an individual engages in exercise.

Figure 2:
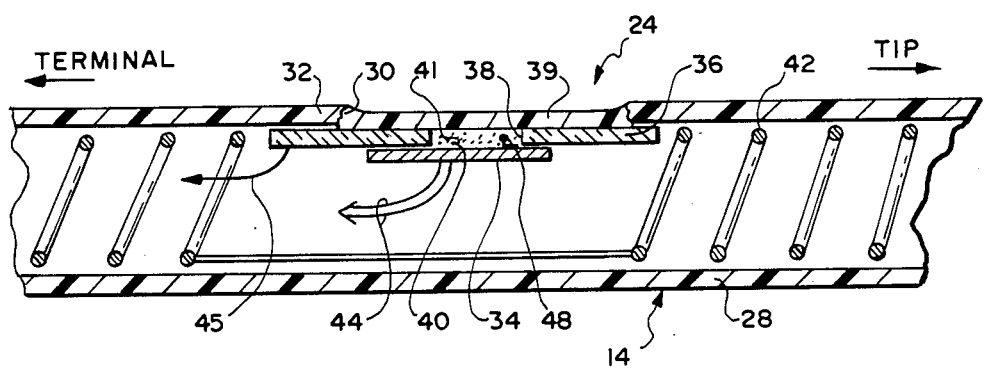
FIG. 2 is a longitudinal sectional view through the pacing lead shown in FIG. 1 and through the sensor mounted in the pacing lead and shows the ISFET sensor mounted within the lead beneath an opening in the lead.

In FIG. 2 there is shown an enlarged longitudinal cross section of the portion of the pacing lead 14 in which the $pCO_2$ sensor 24 is mounted. Here it will be seen that the pacing lead 14 includes a tubular sheath 28 with an opening 30 in the sheath 28. A chip, or ISFET 34 is positioned beneath the opening 30 and secured to the underside of a glass carrier 36 having an opening 38 therein aligned with the opening 30. A $CO_2$-permeable membrane 39, such as a silicone rubber membrane 39, is formed across and seals the opening 30 and is adhered to the glass carrier 36 to form a sealed chamber 40 within the glass carrier 36. A liquid solution 41 is placed in the chamber 40.

Also mounted within the sheath 28 is a conventional coiled wire conductor or filar 42 for conducting sensed pulses or stimulating pulses between the pacer 12 and the tip electrode 20. Also, wire conductors 44 extend from the ISFET 34 through the lumen of the sheath 28 or within the sheath 28 itself to the pacer 12 and a wire conductor 45 extends from the glass carrier 36 through the lumen of the sheath 28 or within the sheath 28 itself to the pacer 12. The wire conductor 45 is adapted to be connected to a reference electrode 48 as illustrated in larger detail in the schematic circuit diagram of the sensor 24 shown in FIG. 3.

Figure 3:
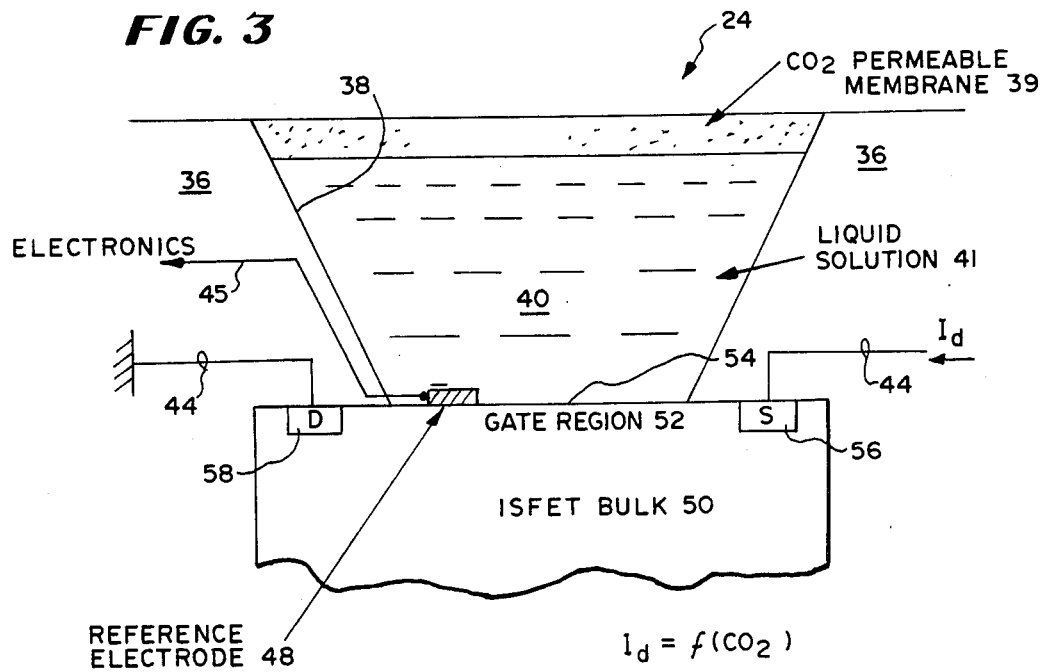
FIG. 3 is an enlarged mechanical and schematic diagram of the sensor shown in the lead of FIG. 2 and shows an ISFET bulk having a gate region/pH electrode in the middle area thereof facing the opening in the pacing lead, the reference electrode, the $CO_2$ permeable membrane, the chamber containing a liquid solution, and the source and drain formed in the ISFET bulk.

As shown in FIG. 3, the ISFET sensor 24 includes a silicon bulk 50 having a gate region 52 in the middle area thereof aligned with the opening 38 in the carrier 36 and facing into the chamber 40. The reference electrode 48 is positioned within the chamber 40 typically in the vicinity of or just above the gate region 52. A source 56 and a drain 58 are formed in the bulk 50.

The source 56 and drain 58 are coupled by the wire conductors 44 to a source of voltage potential so that a current $I_d$ can flow from the source 56 to the drain 58 as modified by the potential of the gate region 52 which is altered by the ionic concentration in the liquid solution 41 which in turn is altered by the amount of free hydrogen ions in the solution 41 as caused by an increase or decrease in the amount of $CO_2$ in the liquid solution 41. The change in $CO_2$ in the liquid solution 41 is directly related to the partial pressure of the carbon dioxide, $pCO_2$, in the blood on the outside of the membrane 39. In other words, $I_d$ is a function of $CO_2$ in the liquid solution 41.

It is believed that the change in pacing rate, $\Delta R$, relative to change in $pCO_2$ can be considered linear and such a representation of this linear relationship of $\Delta R$ to $\Delta pCO_2$ is shown in FIG. 5 where the rate of change is defined by a slope "A" of the graph or curve (straight line 60) shown in FIG. 5.

Figure 4:
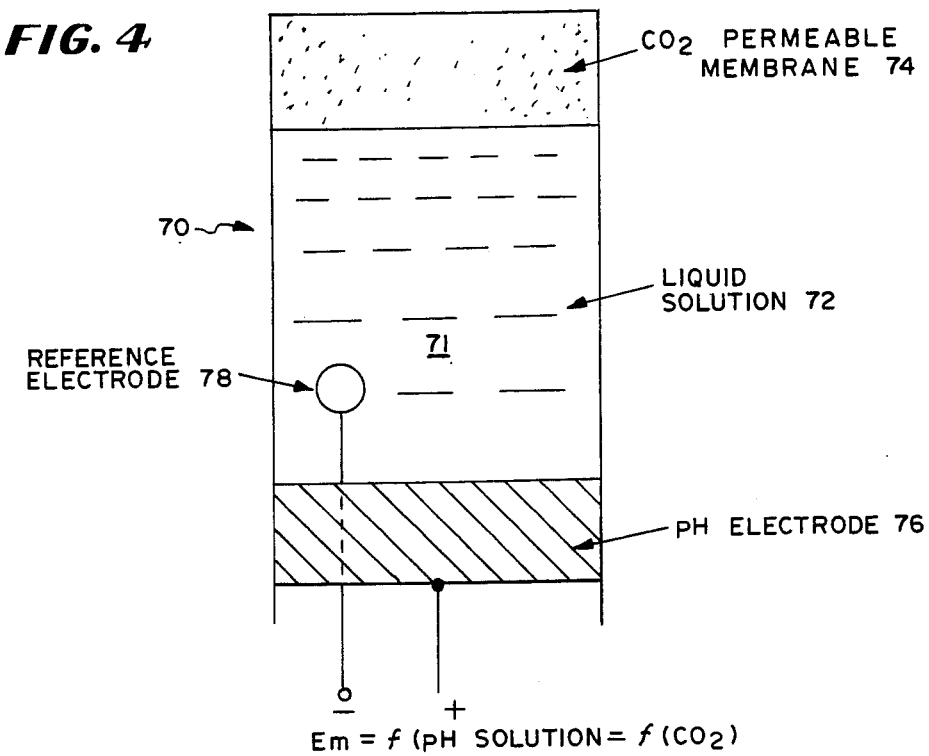
FIG. 4 is a schematic diagram of a $pCO_2$ sensing system and shows a chamber containing a liquid solution with a pH electrode on one side of the chamber, a $CO_2$ permeable membrane at the other side of the chamber, and a reference electrode located within the chamber.

In FIG. 4 is illustrated a $pCO_2$ sensor 70 which can be used in place of the ISFET $pCO_2$ sensor 24. This $pCO_2$ sensor 70 includes a chamber 71 having a liquid solution 72 therein. The chamber 71 has a $CO_2$-permeable membrane 74 on one side thereof and a pH electrode 76 on the other side thereof. A reference electrode 78 such as a solid state reference electrode 78 of the type disclosed in the Zick et al U.S. Pat. No. 4,450,842 is mounted in the chamber 71. Here the voltage or potential between the reference electrode 78 and the pH electrode 76 is a function of the pH of the liquid solution 72 which is directly proportional to and a function of the amount of $CO_2$ in the liquid solution 72. Again, if desired, this form of $pCO_2$ sensor 70 can be utilized in place of the ISFET $pCO_2$ sensor 24.

In the sensor 70 the potential, $E_m$, between electrodes 78 and 76 is a function of the pH in the solution 72 in the sensor 70 which in turn is a function of the carbon dioxide which has diffused from the blood through the membrane 74 into the chamber 71.

Such a $pCO_2$ sensor 70 can comprise wire electrodes or metal electrodes.

Also, it may be possible to use an optical $pCO_2$ sensor in the pacer system 10.

The relationship between the change in $pCO_2$, $\Delta pCO_2$, to the change in heart/pacer rate for a normal heart can be programmed in the form of an algorithm in the memory of the microprocessor or any other control circuitry mounted within the pacer 12. Typically, one will have a patient run on a treadmill to determine his or her relationship between venous blood $pCO_2$ and changes thereof, $\Delta pCO_2$, relative to heart rate R and changes in heart rate, $\Delta R$, by comparing heart rate with measurements of $pCO_2$ in the venous blood for different levels of exercise.

Also, if the $pCO_2$ sensor 24 or 70 should lose some of its sensitivity over time, the pacer system 10 can be reprogrammed via an in vivo calibration of the $pCO_2$ sensor/pacer system utilizing the treadmill exercise procedure.

The $pCO_2$ sensor/pacer system 10 also can be reprogrammed indirectly by adjusting the pacer rate to the treadmill exercise level, instead of the measured exercise-induced $pCO_2$ change.

Also, the current drain of the ISFET $pCO_2$ sensor 24 can be reduced by operating the sensor 24 in a pulsating AC mode of operation rather than in a DC mode of operation. Empirical tests have shown that this may also improve the stability of the ISFET $pCO_2$ sensor 24.

To avoid small oscillations a general filtering principle or an N-point averaging technique is employed. In this respect, an N number of samples between 1 and 10, for example, are made and the average is chosen as the sampled peak partial pressure. Then, this average is compared with the previously stored average of the peak partial pressure value to determine if there has been a change. To simplify this explanation, $pCO_2$ is defined here as simply p. The change then is detected by measuring $\Delta p = p_x - (p_{x-1})$ where x equals the time order for a number of samples, N. Of course, to make this detection more reliable, one would detect, sense and determine $p_x - (p_{x-1})$, $(p_{x-1}) - (p_{x-2})$ and $(p_{x-2}) - p_{x-3}$. As a simplification, when all the differences have the same sign, the change is consistent. Then $\Delta p = p_x - (p_{x-1})$ and that is used as an input for the algorithm stored in the microprocessor within the pacer 12.

The algorithm or routine in its simplest form relates $\Delta R$, which is the change in rate of pulses emitted by the pacer 12, literally to $\Delta pCO_2$, which is the change in partial pressure of $pCO_2$ in the blood in the heart. This can be realized in analog techniques but can also be realized in a digital manner assuming a linear relationship (FIGS. 5 and 6), or using a so-called "look-up" table (FIG. 8). The signal, $pCO_2$, serves as an input to the microprocessor in the pacer 12 which serves to change the pacer rate as a function of $\Delta pCO_2$. Typically, an algorithm relationship of $\Delta pCO_2$ to $\Delta R$, such as shown in FIG. 5 or FIG. 7, is stored in the memory of the microprocessor in the pacer 12, i.e., slope "A" of curve line 60, and the equation therefor, or varying slope "B" of non-linear curve 80 (FIG. 7) and a look-up table which is utilized by the control circuitry.

In the event the sensor 24 or the circuitry within the pacer 12 malfunctions, the control circuitry can be caused to exit the program or routine and convert the pacer to its standard non-exercise responsive function. Furthermore, if the peak partial pressure of $CO_2$ shows oscillation, the number N in the N-point averaging can be programmed or changed to a higher value and the circuitry for sensing or detecting a change in $pCO_2$ can be programmed to take more samplings of differences before it decides that a change in $pCO_2$ has occurred to cause a change in rate.

In utilizing the apparatus 10 as shown in FIG. 1, certain parameters have to be determined experimentally and programmed into the microprocessor within the pacer 12. First of all, the linear relationship between heart rate and $\Delta pCO_2$ between a programmed $\Delta R_{Max.1}$ and a programmed $\Delta R_{Max.2}$ of heart rate changes is established and can be shown as the line having the slope "A" in FIG. 5. $\Delta R_{Max.1}$ is a maximum rate increase allowed whereas $\Delta R_{Max.2}$ is a maximum rate decrease allowed.

The linear graph of $\Delta R$ versus $\Delta pCO_2$ has the equation $\Delta R = A(\Delta pCO_2)$ between the limits $\Delta R_{Max.1}$ and $\Delta R_{Max.2}$. The slope "A", $\Delta R_{Max.1}$ and $\Delta R_{Max.2}$, $R_{Max.}$ (the maximum allowable pacer rate) and $R_{Min.}$ (the minimum allowable pacer rate) are all stored within the pacer's memory. Then, the above formula or algorithm is utilized in the program or routine carried out by the microprocessor in the pacer 12. This routine for a linear or straight line relationship between $\Delta R$ and $\Delta pCO_2$ is set forth in the flow chart shown in FIG. 6.

Figure 6:
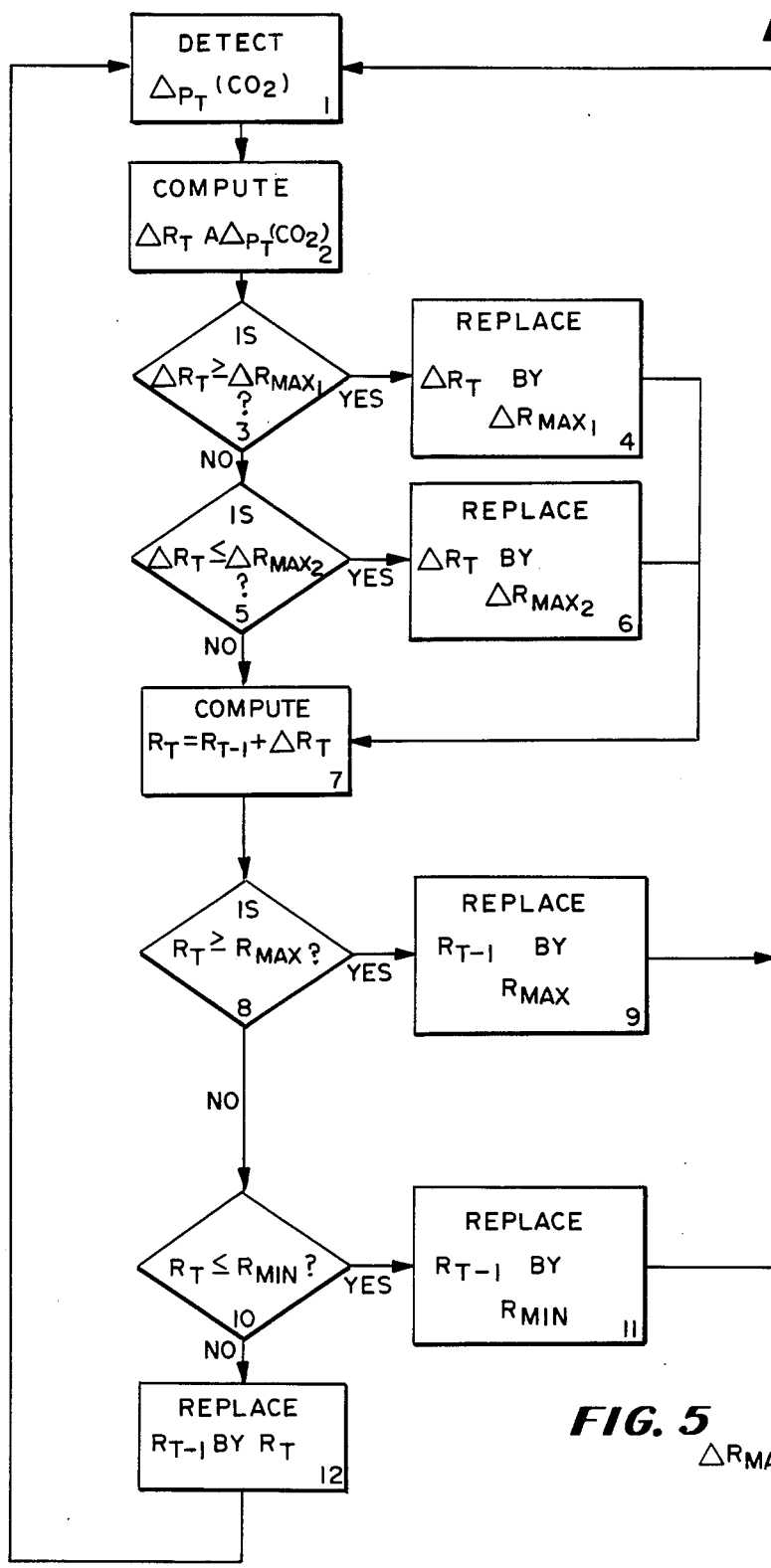
FIG. 6 is a flow chart of the program or routine carried out by the control circuitry (microprocessor) in the apparatus shown in FIG. 1 assuming a linear relationship between $\Delta R$ and $\Delta pCO_2$ as shown in FIG. 5.

The steps carried out by the program or routine shown in FIG. 6 are as follows:

STEP 1. Here the partial pressure change is detected and determined at a sampling time T, and identified as $\Delta p_T CO_2$.

STEP 2. Here $\Delta R$ is computed using the equation: $\Delta R_T = A(\Delta p_T CO_2)$.

STEP 3. At this step, a determination is made whether $\Delta R_T$ is greater than or equal to $\Delta R_{Max.1}$.

STEP 4. If $\Delta R_T$ is greater than or equal to $\Delta R_{Max.1}$, $\Delta R_T$ is replaced by $\Delta R_{Max.1}$ and the program proceeds to STEP 7 for rate computation.

STEP 5. If the pacer rate change is not greater than or equal to $\Delta R_{Max.1}$, at STEP 5 a determination is made if $\Delta R_T$ is less than or equal to $\Delta R_{Max.2}$. If the $\Delta R_T$ is not less than or equal to $\Delta R_{Max.2}$, the program goes to STEP 7. If "yes", it goes to STEP 6.

STEP 6. If $\Delta R_T$ is less than or equal to $\Delta R_{Max.2}$, $\Delta R_T$ is replaced by $\Delta R_{Max.2}$ and the program proceeds to STEP 7.

STEP 7. Here the proposed new pacing rate is computed from $\Delta R_T$ and $R_{T-1}$, which is the previously stored value.

STEP 8. Here a determination is made whether or not $R_T$ is greater than or equal to $R_{Max.}$.

STEP 9. If $R_T$ is equal to or greater than $R_{Max.}$, $R_{T-1}$ is replaced by $R_{Max.}$ and $R_{Max.}$ is used as a new rate value and the program loops back to STEP 1 for a new sampling.

STEP 10. If $R_T$ is less than $R_{Max.}$, a determination is made at STEP 10 whether or not $R_T$ is less than or equal to $R_{Min.}$.

STEP 11. If $R_T$ is less than or equal to $R_{Min.}$, then $R_{T-1}$ is replaced by $R_{Min.}$ and the program loops back to STEP 1 for a new sampling.

STEP 12. If $R_T$ is not less than or equal to $R_{Min.}$, the pacing rate is set to the calculated value of $R_T$ or the closest programmable value and the program returns to STEP 1.

As shown in FIG. 7, the relationship between $\Delta R$ and $\Delta pCO_2$ may not be linear. In such a situation, it is preferable to use a look-up table rather than to determine some formula for the nonlinear slope "B" of the graph shown in FIG. 7.

Thus, with reference to the graph shown in FIG. 7 of $\Delta pCO_2$ versus $\Delta R$ it is possible for the corresponding values of points on the curve or graph having the nonlinear slope "B" to be stored in a memory along with $R_{Max.}$ and $R_{Min.}$ Then, the program or routine carried out by the microprocessor in the pacer 12 is as shown in FIG. 8 and is as follows:

STEP 1. Here $\Delta p_T CO_2$ at a sampling time T is detected.

STEP 2. From the look-up table, $\Delta R_T$ is found.

STEP 3. Here the proposed new pacing rate $R_T$ is calculated from the previously stored value $R_{T-1}$ and $\Delta R_T$.

STEP 4. At this step, a determination is made whether or not the rate $R_T$ is greater than or equal to $R_{Max.}$ STEP 5. If $R_T$ is greater than or equal to $R_{Max.}$, $R_{T-1}$ is replaced by $R_{Max.}$ and the program loops back to STEP 1 for a new sampling.

STEP 6. If $R_T$ is less than $R_{Max.}$, a determination is made if $R_T$ is less than or equal to $R_{Min.}$.

STEP 7. If $R_T$ is less than or equal to $R_{Min.}$, $R_{T-1}$ is replaced by $R_{Min.}$ and the program loops back to STEP 1.

STEP 8. If $R_T$ is greater than $R_{Min.}$, the pacer rate is set equal to the calculated value or the nearest programmable value and the program loops back to STEP 1 for the next sample.

In FIG. 9 is illustrated a schematic circuit diagram for the control circuitry, generally identified by reference numeral 100, which can be provided in the pacer 12 for pacing two heart chambers such as in a DDD pacer where both chambers, the atrium and the ventricle, are paced and spontaneous electrical activity is sensed in both the chambers. Such a pacer has either triggered or inhibited response, depending on the mode programmed by the physician.

The control circuitry 100 includes a microprocessor 102 having connected thereto a ROM 104 and programming receiver/decoder/telemetry circuitry 106.

Also connected to the microprocessor are the inputs from two leads, lead 1 and lead 2, which inputs are amplified by a first amp 1 or a second amp 2. Then outputs from the microprocessor are supplied to each of the leads 1 and 2.

A pCO$_2$ 110 is also coupled to the microprocessor 102 and to one of the leads, such as lead 2, which can be an atrial lead or a ventricular lead.

The output of the pCO$_2$ sensor will be converted by the microprocessor into a corresponding pacer rate which will be supplied to the leads of the pacemaker via the output circuits 1 and 2.

Figure 10:
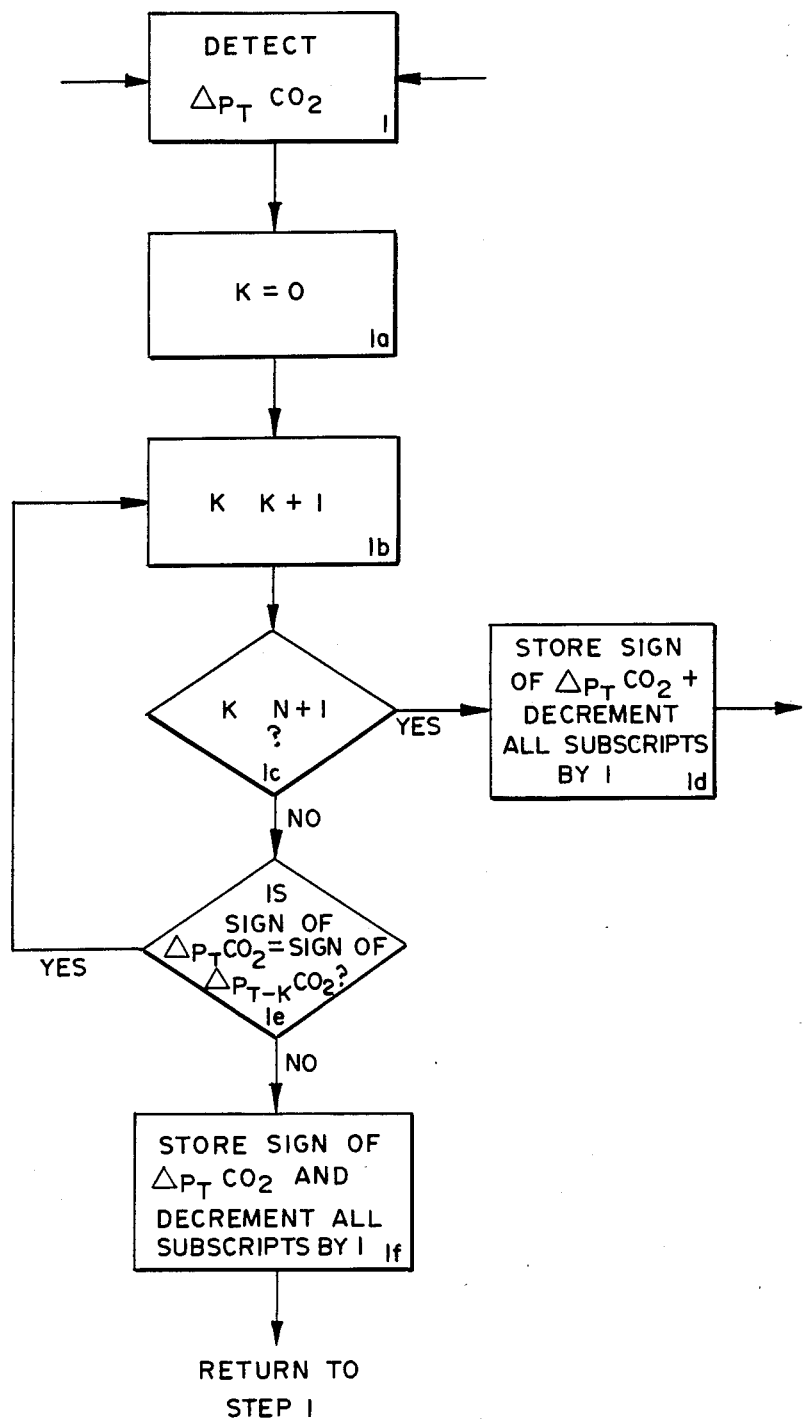
FIG. 10 is a flow chart of a subroutine that can be carried out by the control circuitry (microprocessor) of the apparatus shown in FIG. 1 to provide smoothing of the heart/pacer rate changes by smoothing the changes in $\Delta pCO_2$, and is inserted between steps 1 and 2 of the routine or program shown in FIG. 6 or FIG. 8.

If desired, a smoothing subroutine may be incorporated into the programs or routines shown in FIGS. 6 and 8 and the flow chart for such a subroutine is shown in FIG. 10. This subroutine may be able to protect against various changes in sign of $\Delta p_T CO_2$ by only accepting its value if its sign is the same as that of the N−1 previous samples.

The smoothing subroutine is inserted between STEPS 1 and 2 of either of the routines illustrated in FIG. 6 or FIG. 8.

The steps of this subroutine are as follows

STEPS 1a, 1b and 1c. Here a counting procedure is undertaken where at STEP 1a a count K=0 and at STEP 1b the count is K=K+1 followed by a determination at STEP 1c if K=N+1.

STEP 1d. If K=N+1, the sign of $\Delta p_T CO_2$ is stored and all subscripts are decremented by 1.

STEP 1e. If K is not equal to N+1, a determination is made whether or not the sign of $\Delta p_T CO_2$ equals the sign of $\Delta p_{T-K}(CO_2)$. If the answer is yes, the program loops back to STEP 1b.

STEP 1f. If the answer is no, the sign of $\Delta p_T CO_2$ is stored and all subscripts are decremented by 1. From STEP 1f, the program loops back to STEP 1.

From the foregoing description, it will be apparent that the apparatus 10 of the present invention and the method for using same provide a simple and practical means for adjusting the pacing rate of a pacing system relative to changes in partial pressure of carbon dioxide, pCO$_2$, in the blood in the heart as a patient with the implanted pacer system 10 is undergoing exercise.

Also, it will be apparent that modifications can be made to the apparatus and method of the present invention without departing from the teachings of the invention. Accordingly, the scope of the invention is only to be limited as necessitated by the accompanying claims.

We claim:

1. An implantable apparatus for pacing a heart in accordance with the heart/pacer rate needed to produce a required cardiac output relative to the partial pressure of carbon dioxide in blood, pCO$_2$, while the person having the apparatus implanted within his body is exercising comprising:

a demand pacer for implantation in the human body and having a pulse generator and control circuitry mounted therein and operable to sense, through a pacing lead, when a heart is not naturally paced;

a pacing lead for implantation in a heart and coupled to said pacer, said pacing lead having a tip electrode for engaging and supplying pacing pulses to a ventricle of a heart and having an opening therein which is located in a portion of the lead which is received in a heart chamber when the lead is implanted in a heart;

pCO$_2$ sensing means mounted in said opening for sensing the partial pressure (tension) of CO$_2$ dissolved in the blood and generating signals related to the pCO$_2$ sensed; and said control circuitry comprising a microprocessor including means for relating a signal from the pCO$_2$ sensing means to the partial pressure of carbon dioxide, pCO$_2$, in the blood, means for determining changes in the partial pressure of carbon dioxide, $\Delta p_T CO_2$, and relating such changes to a corresponding change in pacing rate, $\Delta R_T$, between a maximum rate increase allowed, $\Delta R_{Max.1}$, and a maximum rate decrease allowed, $\Delta R_{Max.2}$, means for adjusting the pacing rate, $\Delta R_{T-1}$, by adding $\Delta R_T$ to the present pacing rate, $R_{T-1}$, to obtain a new pacing rate, $R_T$, between a minimum programmed pacing rate, $R_{Min.}$ and a maximum programmed pacing rate, $R_{Max.}$, needed to supply a required cardiac output relative to the pCO$_2$ measured, and means for causing the pacer to pace the heart at the newly calculated required rate when the heart is not naturally paced while the person is exercising.

2. The apparatus of claim 1 wherein said control circuitry comprises memory means having as look-up table therein of the relationship between $\Delta R_T$ and $\Delta p_T CO_2$ and means for adjusting the pacing rate, $R_{T-1}$, including means for computing $R_T$ from reference to the look-up table for a $\Delta R_T$ corresponding to a calculated $\Delta p_T CO_2$, at a particular point in time for a measurement a $pCO_2$ during exercise.

3. The apparatus of claim 2 wherein said control circuitry includes means for smoothing out changes in $\Delta p_T CO_2$ and means for determining when there has been a change in sign between samplings of $pCO_2$ and calculations of $\Delta p_T CO_2$.

4. The apparatus of claim 1 wherein said $pCO_2$ sensing means comprises an ion sensitive field effect transistor (ISFET) which is mounted in the pacing lead beneath the opening and which includes:

a silicon bulk having a middle surface area defining a gate region of aid ISFET and facing the opening;

means forming side walls for a chamber above said gate region;

a liquid solution in said chamber over the gate region;

a $CO_2$ permeable membrane across the opening and the gate region sealing off the area above the gate region to hold the liquid solution in said chamber formed between the bulk and the membrane above the gate region;

a drain formed in the silicon bulk;

a source formed in the silicon bulk; and a reference electrode mounted in the chamber;

and means for supplying voltage to said ISFET and to said reference electrode whereby the drain-source current through the ISFET (assuming the voltage between reference electrode and source is kept constant) is changed by free hydrogen ions in the liquid solution caused by $CO_2$ that passes from the blood through the permeable membrane into the liquid solution, such changer in drain-source current is directly related to the $pCO_2$ in the blood in the heart.

5. The apparatus of claim 1 wherein said control circuitry comprises memory means having a look-up table of required heart rate changes relative to various values of $pCO_2$ changes, an algorithm for operating said apparatus stored therein, and a microprocessor including:

means for meausring the $pCO_2$ sensed at a first point in time;

means for computing the incremental change in $pCO_2$;

$$\Delta pCO_2 = pCO_{2T} - (pCO_{2T-1});$$

means for looking up the corresponding $\Delta R_T$ in the look-up table;

means for computing the required heasrt rate $R_T = \Delta R + (R_{T-1})$;

means for determining whether the computed heart rate, $R_T$, is equal to or above the maximum programmed pacer rate, $R_{Max}$, or is equal to or below the minimum programmed pacer rate, $R_{Min}$; and means for replacing the pacer rate $R_{T-1}$ by either the maximum programmed pacer rate, $R_{Max}$, or minimum programmed pacer rate, $R_{Min}$, stored in the memory of the microprocessor and replacing the last sensed $pCO_2$ value with the newly sensed $pCO_2$ value if the calculated heart rate meets either of the two conditions set forth above;

means for replacing the last pacing rate, $R_{T-1}$, by the newly computed heart rate, $R_T$, and replacing the last $pCO_2$ by the newly measured $pCO_2$, if the heart rate, $R_T$, calculated is between the maximum, $R_{Max}$, and minimum, $R_{Min}$, pacer rates stored in the memory of the microprocessor, and means for adjusting the pacer rate to the value of the heart rate just calculated.

6. An implantable apparatus for pacing a heart in accordance with the heart/pacer rate needed to produce a required cardiac output relative to the partial pressure of carbon dioxide in the blood, $pCO_2$, while the person having the apparatus implanted within his body is exercising comprising:

a demand pacer for implantation in the human body and having a pulse generator and control circuitry mounted therein and operable to sense, through a pacing lead, when a heart is not naturally paced;

a pacing lead for implantation in a heart and coupled to said pacer, said pacing lead having a tip electrode adapted to engage and supply pacing pulses to a ventricle of the heart when the lead is placed in a heart and having an opening therein which is located in a portion of the lead which is received in a heart chamber when the lead is placed in a heart;

said opening containing a $pCO_2$ sensor comprising a $CO_2$ permeable membrane which will make contact with the blood in a heart when the lead is placed in a heart and forming one side of a chamber having a liquid solution therein, a pH electrode on the other side of said chamber, a solid state reference electrode positioned within said chamber, and means for supplying voltage to said pH electrode and to said reference electrode whereby the potential between said pH electrode and said reference electrode is changed by the amount of free hydrogen ions in the liquid solution and such change in potential is directly related to the $pCO_2$ of the blood in a heart; and said control circuitry comprising a microprocessor for relating the drain-source current to the partial pressure of carbon dioxide, $pCO_2$, in the blood, means for determining changes in the partial pressure of carbon dioxide, $\Delta pCO_2$, and relating such changes to a corresponding change in pacing rate, $\Delta R_T$, between a maximum rate increase allowed, $R_{Max.1}$, and a minimum rate decrease allowed, $R_{Max.2}$, means for adjusting the pacing rate, $R_{T-1}$, by adding $\Delta R_T$ to the present pacing rate, $R_{T-1}$, to obtain a new pacing rate, $R_T$, between a minimum programmed pacing rate, $R_{Min}$, and a maximum programmed pacing rate, $R_{Max}$, needed to supply a desired cardiac output relative to the $pCO_2$ measured, and means for causing the pacer to pace the heart at the newly calculated required rate when the heart is not naturally paced while the person is exercising.

7. The apparatus of claim 6 wherein said control circuitry includes a memory having a look-up table therein of the relationship between $\Delta R_T$ and $\Delta p_T CO_2$ and said control circuitry includes means for computing $R_T$, by referencing the look-up table for a $\Delta R_T$ corresponding to a calculated $\Delta p_T CO_2$, at a particular point in time for a measurement of $pCO_2$ during exercise.

8. The apparatus of claim 6 wherein said control circuitry includes means for smoothing changes in $\Delta p_T CO_2$ and means for determining when there has been a change in sign between samplings of $pCO_2$ and calculations of $\Delta p_T CO_2$ so that samplings can be restarted after a change in direction, up or down, of the changes in $pCO_2$.

9. The apparatus of claim 6 wherein said control circuitry comprises memory means having as look-up table of required pacing rates relative to various values of $pCO_2$ and an algorithm for operating said apparatus stored therein, and a microprocessor including:
 means for measuring the $pCO_2$ sensed;
 means for looking up the corresponding heart rate in the look-up table;
 means for adjusting the pacer rate to the value looked up in the look-up table; and
 means for monitoring and repeating the step of measuring $pCO_2$ and changing the pacing rate as the $pCO_2$ changes.

10. A method for pacing a heart in accordance with the heart rate needed to produce a required cardiac output relative to the partial pressure of carbon dioxide in the blood, $pCO_2$, while a person, whose heart is being paced, is exercising, said method comprising the steps of:
 implanting a demand pacer in a human body having a pulse generator and control circuit mounted therein;
 implanting a pacing lead in a heart and coupling said lead to said pacer, said pacing lead having a tip electrode;
 positioning said tip electrode to engage in and supply pacing pulses to a ventricle of the heart;
 providing said pacing lead with an opening therein a portion of the lead which is received in the heart;
 mounting $pCO_2$ sensing means in the opening in the lead;
 sensing the $pCO_2$ in the heart with the $pCO_2$ sensing means;
 determining with said control circuitry the partial pressure of carbon dioxide, $pCO_2$, in the blood from signals from asid $PCO_2$ sensing means;
 determining the required pacing rate needed to supply a desired cardiac output relative to the sensed $pCO_2$ including the steps of:
 determining values of $pCO_2$ sensed;
 determining changes in $pCO_2$ sensed;
 relating the change, $\Delta p_T CO_2$, to a corresponding change in heart rate, $\Delta R_T$, between a maximum rate increase allowed, $R_{Max.1}$, and a minimum rate decrease allowed, $R_{Max.2}$;
 adjusting the pacing rate, $R_{T-1}$, by adding $\Delta R_T$ to the present pacing rate, $R_{T-1}$, to obtain a new pacing rate, $R_T$, between a minimum programmed pacing rate, $R_{Min}$, and a maximum programmed pacing rate, $R_{Max}$; and
 causing the pacer to pace the heart at the newly calculated required pacing rate, $R_T$, when the heart is not naturally paced.

11. The method of claim 10 wherein said step of relating partial pressure of carbon dioxide to changes in heart rate, $\Delta R_T$, and determining the required pacing rate includes looking up in a look-up table in a memory the relationship between $\Delta R_T$ and $\Delta p_T CO_2$ and said step of relating $pCO_2$ with a required heart rate includes the step of computing $R_T$ by first referencing the look-up table to find a $\Delta R_T$ corresponding to a measured $\Delta p_T CO_2$, at a particular point in time during exercise.

12. The method of claim 10 including the steps of: smoothing changes in $\Delta p_T CO_2$; and determining when there has been a change in sign between samplings of $pCO_2$ so that samplings can be restarted after a change in direction, up or down, of the changes in $pCO_2$.

13. The method of claim 10 including the step of supplying an alternating a current to said $pCO_2$ sensor to minimize power consumption by the $pCO_2$ sensor.

14. The method of claim 10 including the step of supplying pulses of current to said $pCO_2$ sensor to minimize power consumption by the $pCO_2$ sensor.

15. The method of claim 10 wherein said step of relating the $pCO_2$ with the required heart rate comprises the steps of:
 measuring the $pCO_2$ at a first point in time;
 computing the incremental change in $pCO_2$;

$$\Delta pCO_2 = pCO_2 T - (pCO_2 T_{-1});$$

looking up the coresponding $\Delta R$ in a look-up table of heart rates relative to various values of $pCO_2$;
 computing the required heart rate $R_T = \Delta R + (R_{T-1})$;
 determining whether the computed heart rate is equal to or above the maximum programmed pacer rate or is equal to or below the minimum programmed pacer rate; and
 if the calculated heart rate meets either of these conditions, replacing the pacer rate $R_{T-1}$ by either the maximum programmed pacer rate or minimum programmed pacer rate stored in a memory and replacing the last sensed $pCO_2$ with the newly sensed $pCO_2$ value;
 if the heart rate calculated is between the maximum and minimum programmed pacer rates stored in a memory, replacing the last pacing rate by the newly computed heart rate and replacing the last $pCO_2$ value by the newly measured $pCO_2$ value; and then
 adjusting the pacer rate to the value of the pacer rate just calculated.

16. The method of claim 15 including the step of smoothing changes in $\Delta pCO_2$; and determining whether there has been a change in sign between samplings of $\Delta p_T CO_2$ so that samplings can be restarted after a change in direction, up or down, of the changes in $pCO_2$.

17. The method of claim 10 wherein said step of relating $pCO_2$ with the required heart rate comprises the steps of:
 measuring $pCO_2$ in the right ventricle;
 looking up the corresponding heart rate in a look-up table of heart rates relative to various values of $pCO_2$;
 then adjusting the pacer rate to the value looked up in the look-up table; and
 monitoring and repeating the step of measuring $pCO_2$ and changing the pacing rate as the $pCO_2$ changes.

18. A method for pacing a heart in accordance with the heart rate needed to produce a required cardiac output, while a person, whose heart is being paced, is exercising, relative to the partial pressure of carbon dioxide in blood, $pCO_2$, said method comprising the steps of:
 implanting a demand pacer in a human body and having a pulse generator and control circuitry mounted therein;

implanting a pacing lead in a heart and coupling said lead to said pacer, said pacing lead having a tip electrode;

positioning said tip electrode to engage in and supply pacing pulses to a ventricle of the heart;

providing said pacing lead with an opening therein in a portion of the lead which is received in the heart;

mounting a $pCO_2$ sensor in said opening comprising a chamber having a liquid solution therein, a $CO_2$ permeable membrane on one side of said chamber which will make contact with the blood in a heart when the lead is placed in a heart, a pH electrode on the other side of said chamber, a solid state reference electrode positioned within said chamber, and, means for supplying a voltage to said pH electrode and to said reference electrode whereby the potential between said pH electrode and said reference electrode is changed by the amount of free hydrogen ions in the liquid solution and such change in potential is directly related to the $pCO_2$ of the blood in the heart;

sensing the $pCO_2$ in the heart with the $pCO_2$ sensor; and determining with said control circuitry the drain-source current to the partial pressure of carbon dioxide, $pCO_2$, in the blood;

determining the required pacing rate needed to supply a desired cardiac output relative to the sensed $pCO_2$ including the steps of:

determining values of $pCO_2$ sensed;

determining changes in $pCO_2$ sensed relating the change, $\Delta p_T CO_2$, to a corresponding change in heart rate, $\Delta R_T$, between a maximum rate increase allowed, $R_{Max.1}$, and a maximum rate decrease allowed, $R_{Max.2}$;

adjusting the pacing rate, $R_{T-1}$, by adding $\Delta R_T$ to the present pacing rate, $R_{T-1}$, to obtain a new pacing rate, $R_T$, between a minimum programmed pacing rate, $R_{Min.}$, and a maximum programmed pacing rate, $R_{Max.}$; and causing the pacer to pace the heart at the newly calculated required pacing rate, $R_T$, when the heart is not naturally paced.

19. The method of claim 18 wherein said step of relating $pCO_2$ sensed with a required heart rate includes looking up in a look-up table of the relationship between $\Delta R_T$ and $\Delta p_T CO_2$ in a memory and said step of relating $pCO_2$ with a required heart rate including the step of computing $R_T$ from a $\Delta R_T$ corresponding to a measured $\Delta p_T CO_2$ by referencing the look-up table at a particular point in time during exercise.

20. The method of claim 18 including the steps of smoothing changes in $pCO_2$; and determining when there has been a change in sign between samplings of $\Delta p_T CO_2$ so that samplings can be restarted after a change in direction, up or down, of the changes in $pCO_2$.

21. The method of claim 18 including the step of supplying an alternating current to said $pCO_2$ sensor, including said pH electrode and said reference electrode, to minimize the power consumption by the $pCO_2$ sensor.

22. The method of claim 18 including the step of supplying pulses of current to said $pCO_2$ sensor, including said pH sensor and said reference electrode to minimize the power consumption by the $pCO_2$ sensor.

* * * * *

UNITED STATES PATENT AND TRADEMARK OFFICE
CERTIFICATE OF CORRECTION

PATENT NO. : 4,716,887

DATED : January 5, 1988

INVENTOR(S) : Gerrit Koning & Edward A. Schroeppel

It is certified that error appears in the above-identified patent and that said Letters Patent is hereby corrected as shown below:

Column 13, Line 21, "aid" should be --said--

Column 13, Line 41, "changer" should be --change--

Column 13, Line 49, "meausring" should be --measuring--

Column 13, Line 58, "heasrt" should be --heart--

Column 15, Line 7, "as" should be --a--

Column 15, Line 33, after "therein" insert --in--

Column 15, Line 41, "asid" should be --said--

Signed and Sealed this

Twenty-eighth Day of April, 1992

Attest:

HARRY F. MANBECK, JR.

*Attesting Officer*  *Commissioner of Patents and Trademarks*